United States Patent [19]

Pohl et al.

[11] Patent Number: 4,846,998
[45] Date of Patent: Jul. 11, 1989

[54] CYCLOHEXANE DERIVATIVES

[75] Inventors: Ludwig Pohl, Darmstadt; Bernhard Scheuble, Yokohama; Reinhard Hittich, Modautal; Rudolf Eidenschink, Münster; Hans A. Kurmeier, Seeheim-Jugenheim; Andreas Wächtler, Griesheim, all of Fed. Rep. of Germany

[73] Assignee: Merck Patent Gesellschaft Mit Beschränkter Haftung, Darmstadt, Fed. Rep. of Germany

[21] Appl. No.: 5,191

[22] PCT Filed: Mar. 21, 1986

[86] PCT No.: PCT/EP86/00164
§ 371 Date: Nov. 21, 1986
§ 102(e) Date: Nov. 21, 1986

[87] PCT Pub. No.: WO86/05486
PCT Pub. Date: Sep. 25, 1986

[30] Foreign Application Priority Data

Mar. 22, 1985 [DE] Fed. Rep. of Germany ....... 3510432

[51] Int. Cl.$^4$ .................... G02F 1/13; C09K 19/30
[52] U.S. Cl. .................... 252/299.63; 252/299.61; 252/299.62; 252/299.5; 350/35 DR; 350/35 DS; 544/242; 544/298; 549/20; 549/21; 549/22; 549/369; 549/372; 549/373; 549/374; 549/375; 570/127; 570/128; 570/131; 570/183; 570/187; 570/129; 570/130; 570/182; 570/184; 570/188; 558/411; 558/414; 558/417; 558/425; 558/426; 558/415; 558/416; 558/428; 558/430; 558/431; 568/632; 568/634; 568/642; 568/647; 568/631; 568/657; 568/658; 568/659; 568/664; 568/665

[58] Field of Search .................... 350/350 R, 350.5; 252/299.5, 299.6, 299.61, 299.62, 299.63

[56] References Cited

U.S. PATENT DOCUMENTS

| 4,406,814 | 9/1983 | Ferrato et al. ............... 252/299.63 |
| 4,510,069 | 4/1985 | Eidenschink et al. ......... 252/299.63 |
| 4,600,528 | 7/1986 | Eidenschink et al. ......... 252/299.62 |
| 4,622,163 | 11/1986 | Huynh-Ba et al. ............ 252/299.63 |
| 4,627,923 | 12/1986 | Eidenschink et al. ......... 252/299.63 |
| 4,629,581 | 12/1986 | Boller et al. ................ 252/299.61 |
| 4,659,499 | 4/1987 | Ferrato ....................... 252/299.63 |
| 4,684,477 | 8/1987 | Sucimori et al. ............ 252/299.61 |
| 4,704,227 | 11/1987 | Krause et al. ............... 252/299.61 |
| 4,707,295 | 11/1987 | Poal et al. ................... 252/299.63 |
| 4,715,984 | 12/1987 | Krause et al. ............... 252/299.61 |
| 4,723,005 | 2/1988 | Huynh-Ba et al. ............ 252/299.63 |
| 4,726,911 | 2/1988 | Krause et al. ............... 252/299.61 |

FOREIGN PATENT DOCUMENTS

| 63003 | 10/1982 | European Pat. Off. ....... 252/299.63 |
| 3407013 | 9/1985 | Fed. Rep. of Germany ......... 252/299.63 |
| 3506446 | 8/1986 | Fed. Rep. of Germany ......... 252/299.61 |
| 3510434 | 9/1986 | Fed. Rep. of Germany ......... 252/299.61 |

Primary Examiner—Teddy S. Gron
Attorney, Agent, or Firm—Millen, White & Zelano

[57] ABSTRACT

Cyclohexane derivatives of the formula I $$R^1-A^1-Z^1-A^2-R^2 \qquad \text{I}$$

in which $R^1$ and $R^2$ are each an alkyl group having 1–10 C atoms, in which one or two non-adjacent $CH_2$ groups can also be replaced by O atoms and/or —CO— groups and/or —CO—O— groups and/or —CH=CH— groups, one of the radicals $R^1$ and $R^2$ also being H, F, Cl, Br, CN or $R^3-A^3-Z^2$—, $A^1$ is —A—, $A^4$—A— or —A—$A^4$—, A is a trans-1,4-cyclohexylene group which can be substituted in the 2-, 3-, 5- and/or 6-position one or more times by F and/or Cl and/or Br and/or CN and/or an alkyl group or a fluorinated alkyl group which each have 1–10 C atoms and in which one or two non-adjacent $CH_2$ groups can also be replaced by 0 atoms and/or —CO— groups and/or —CO—O— groups, and which may also be substituted in the 1- and/or 4-position, $A^2$, $A^3$ and $A^4$ are each 1,4-phenylene which is unsubstituted or substituted by one or two F and/or Cl atoms and/or $CH_3$ groups and/or CN groups and in which one or two CH groups can also be replaced by N atoms and/or NO; 1,4-cyclohexylene in which one or two non-adjacent $CH_2$ groups can also be replaced by 0 atoms; or 1,3-dithiane-2,5-diyl, piperidine-1,4-diyl, 1,4-bicyclo-(2,2,2)octylene, decahydronaphthalene-2,6-diyl or 1,2,3,4-tetrahydronaphthalene-2,6-diyl groups, $Z^1$ and $Z^2$ are each —CO—O—, —O—CO—, —$CH_2CH_2$—, —$OCH_2$—, —$CH_2O$ or a single bond, and $R^3$ is H, an alkyl group having 1–10 (sic), in which one or two non-adjacent $CH_2$ groups can also be replaced by 0 atoms and/or —CO— groups and/or —CO—O— groups and/or CH=CH— groups, or is F, Cl, Br or CN, with the proviso that in the case of $Z^1$=—CO—O— $A^1$ carries no equatorial substituent in the β-position relative to the —CO—O—bridge, are suitable for use as components of liquid-crystalline phases.

8 Claims, No Drawings

CYCLOHEXANE DERIVATIVES

The invention relates to cyclohexane derivatives of the formula I $$R^1\text{-}A^1\text{-}Z^1\text{-}A^2\text{-}R^2 \qquad I$$

in which $R^1$ and $R^2$ are each an alkyl group having 1–10 C atoms, in which one or two non-adjacent $CH_2$ groups can also be replaced by O atoms and/or —CO— groups and/or —CO—O— groups and/or —CH=CH— groups, one of the radicals $R^1$ and $R^2$ also being H, F, Cl, Br, CN or $R^3\text{-}A^3\text{-}Z^2\text{-}$, $A^1$ is -A-, $A^4$-A- or -A-$A^4$-, A is a trans-1,4-cyclohexylene group which can be substituted in the 2-, 3-, 5- and/or 6-position one or more times by F and/or Cl and/or Br and/or CN and/or an alkyl group or a fluorinated alkyl group which each have 1–10 C atoms and in which one or two non-adjacent $CH_2$ groups can also be replaced by O atoms and/or —CO— groups and/or —CO—O— groups, and which may also be substituted in the 1- and/or 4-position, $A^2$, $A^3$ and $A^4$ are each 1,4-phenylene which is unsubstituted or substituted by one or two F and/or Cl atoms and/or $CH_3$ groups and/or CN groups and in which one or two CH groups can also be replaced by N atoms and/or NO; 1,4-cyclohexylene in which one or two non-adjacent $CH_2$ groups can also be replaced by 0 atoms; or 1,3-dithiane-2,5-diyl, piperidine-1,4-diyl, 1,4-bicyclo-(2,2,2)octylene, decahydronaphthalene-2,6-diyl or 1,2,3,4-tetrahydronaphthalene-2,6-diyl groups, $Z^1$ and $Z^2$ are each —CO—O—, —O—CO—, —$CH_2CH_2$—, —$OCH_2$—, —$CH_2O$— or a single bond, and $R^3$ is H, an alkyl group having 1–10 (sic), in which one or two non-adjacent $CH_2$ groups can also be replaced by 0 atoms and/or —CO— groups and/or —CO—O— groups and/or —CH=CH— groups, or is F, Cl, Br or CN, with the proviso that in the case of $Z^1 =$ —CO—O— $A^1$ carries no equatorial substituent in the $\beta$-position relative to the —CO—O— bridge.

In what follows, Phe is a 1,4-phenylene group, Cy is a 1,4-cyclohexylene group, Dio is a 1,3-dioxane-2,5-diyl group, Bi is a bicyclo-(2,2,2)-octylene group, Pip is piperidine-1,4-diyl group, Pyr is a pyrimidine-2,5-diyl group, Pyn is a pyridazine-3,6-diyl group which may also be present as an N-oxide, Dit is a 1,3-dithiane-2,5-diyl group and Dec is a decahydronaphthalene-2,6-diyl group.

Similar compounds are known for example from German Pat. No. 2,636,684. The compounds specified there, however, unlike the present compounds, contain no trisubstituted cyclohexane rings. Derivatives of trans-4-substituted r-2-methylcyclohexanecarboxylic acid are known from European Offenlegungsschrift 0,063,003. However, it became evident that the derivatives according to the invention of 2-methylcyclohexanecarboxylic acid having an axial methyl group in the $\beta$-position relative to the —CO—O— bridge have a more favorable phase behavior.

The compounds of the formula I can be used like similar compounds as components of liquid-crystalline dielectrics, in particular for displays which are based on the principle of the twisted cell, the guest-host effect, the effect of deformation of aligned phases or the effect of dynamic scattering.

The invention has for its object to find new stable liquid-crystalline or mesogenic compounds which are suitable for use as components of liquid-crystalline phases.

It was found that the compounds of the formula I are highly suitable for use as components of liquid-crystalline phases. In particular, they can be used to prepare stable liquid-crystalline phases of very low optical anisotropy and comparatively low viscosity.

Providing the compounds of the formula I also has the very general effect of considerably widening the range of liquid-crystalline substances which, from various application aspects, are suitable for preparing nematic mixtures.

The compounds of the formula I have a broad range of application. Depending on the choice of substituents, these compounds can serve as base materials of which liquid-crystalline phases are predominantly composed; however, it is also possible to add compounds of the formula I to liquid-crystalline base materials from other classes of compounds, for example in order to reduce the dielectric and/or optical anisotropy of such a dielectric and/or to suppress interfering smectic phase ranges. The compounds of the formula I are further suitable for use as intermediates for preparing other substances which can be used as constituents of liquid-crystalline phases.

The compounds of the formula I are colorless in the pure state and form liquid-crystalline mesophases in a temperature range which is suitable for electro-optical use. They are very stable chemically, thermally and to light.

The invention thus provides compounds of the formula I and a process for their preparation, characterized in that a compound which otherwise conforms to the formula I but in place of H atoms contains one or more reducible groups and/or C—C bonds is treated with a reducing agent, or in that, to prepare esters of the formula I, an appropriate carboxylic acid or one of its derivatives of appropriate reaction is reacted with an appropriate alcohol or one of its reactive derivatives, or in that, to prepare dioxane derivatives of the formula I, an appropriate aldehyde is reacted with an appropriate diol, or in that, to prepare nitriles of the formula I, an appropriate carboxamide is dehydrated or an appropriate carbonyl halide is reacted with sulfamide.

The invention further provides the use of the compounds of the formula I as components of liquid-crystalline phases. The invention also provides liquid-crystalline phases containing at least one compound of the formula I and also liquid crystal display elements, in particular electro-optical display elements, which contain such phases.

Heretofore and hereinafter, $R^1$, $R^2$, $R^3$, $A^1$, $A^2$, $A^3$, $A^4$, A, $Z^1$ and $Z^2$ have the specified meaning, unless expressly stated otherwise.

The compounds of the formula I correspondingly comprise in particular compounds of the part formulae Ia and Ib (with two rings)

$$R^1\text{-A-}A^2\text{-}R^2 \qquad Ia$$

$$R^1\text{-A-}Z^1\text{-}A^2\text{-}R^2 \qquad Ib$$

Ic to Ii (with three rings),

| | |
|---|---|
| $R^1$-$A^4$-A-$A^2$-$R^2$ | Ic |
| $R^1$-A-$A^4$-$A^2$-$R^2$ | Id |
| $R^1$-A-$A^4$-$Z^1$-$A^2$-$R^2$ | Ie |
| $R^1$-A-$A^4$-$Z^1$-$A^2$-$R^2$ | If |
| $R^1$-A-$Z^1$-$A^2$-$A^3$-$R^3$ | Ig |
| $R^3$-$A^3$-$Z^2$-A-$Z^1$-$A^2$-$R^2$ | Ih |
| $R^1$-A-$Z^1$-$A^2$-$Z^2$-$A^3$-$R^3$ | Ii | and also Ij to It (with four rings)

| | |
|---|---|
| $R^1$-$A^4$-A-$A^2$-$A^3$-$R^3$ | Ij |
| $R^1$-A-$A^4$-$A^2$-$A^3$-$R^3$ | Ik |
| $R^3$-$A^3$-$Z^2$-$Z^4$-A-$A^2$-$R^2$ | Il |
| $R^3$-$A^3$-$A^4$-A-$Z^1$-$A^2$-$R^2$ | Im |
| $R^1$-A-$A^4$-$A^2$-$Z^2$-$A^3$-$R^3$ | In |
| $R^1$-A-$A^4$-$Z^1$-$A^2$-$A^3$-$R^3$ | Io |
| $R^1$-$A^4$-A-$Z^1$-$A^2$-$A^3$-$R^3$ | Ip |
| $R^1$-$A^4$-A-$Z^1$-$A^2$-$Z^2$-$A^3$-$R^3$ | Iq |
| $R^1$-A-$A^4$-$Z^1$-$A^2$-$Z^2$-$A^3$-$R^3$ | Ir |
| $R^3$-$A^3$-$Z^2$-$A^4$-A-$Z^1$-$A^2$-$R^2$ | Is |
| $R^3$-$A^3$-$Z^2$-A-$A^4$-$Z^1$-$A^2$-$R^2$ | It |

Of these, those of the formulae Ia, Ib, Ic, Id, Ie, If, Ig, Ij and Ik are particularly preferred.

The preferred compounds of the formula Ia comprise those of the part formulae Ia1 and Ia3:

| | |
|---|---|
| $R^1$-A-Ph-$R^2$ | Ia1 |
| $R^1$-A-Cy-$R^2$ | Ia2 |
| $R^1$-A-Bi-$R^2$ | Ia3 |

Of these, those of the part formulae Ia1 and Ia2 are particularly preferred.

The preferred compounds of the formula Ib comprise those of the part formulae Ib1 to Ib3:

| | |
|---|---|
| $R^1$-A-$Z^1$-Ph-$R^2$ | Ib1 |
| $R^1$-A-$Z^1$-Cy-$R^2$ | Ib2 |
| $R^1$-A-$Z^1$-Bi-$R^2$ | Ib3 |

Of these, those of the part formulae Ib1 and Ib2, in particular those in which $Z^1$ is —CO—O—, —O—CO— or —CH$_2$CH$_2$—, are particularly preferred.

The preferred compounds of the formula Ic comprise those of the part formulae Ic1 and Ic2:

| | |
|---|---|
| $R^1$-Cy-A-Cy-$R^2$ | Ic1 |
| $R^1$-Cy-A-Ph-$R^2$ | Ic2 |

The preferred compounds of the formula Id comprise those of the part formulae Id1 to Id4:

| | |
|---|---|
| $R^1$-A-Cy-Cy-$R^2$ | Id1 |
| $R^1$-A-Ph-Ph-$R^2$ | Id2 |
| $R^1$-A-Ph-Cy-$R^2$ | Id3 |
| $R^1$-A-Cy-Ph-$R^2$ | Id4 |

The preferred compounds of the formula Ie comprise those of the part formulae Ie1 to Ie3:

| | |
|---|---|
| $R^1$-Cy-A-$Z^1$-Cy-$R^2$ | Ie1 |
| $R^1$-Cy-A-$Z^1$-Ph-$R^2$ | Ie2 |
| $R^1$-Ph-A-$Z^1$-Cy-$R^2$ | Ie3 |

Of these, those of the part formulae Ie1, in particular those in which $Z^1$ is —CO—O—, —O—CO— or —CH$_2$CH$_2$—, are particularly preferred.

The preferred compounds of the formula If comprise those of the part formulae If1 to If4:

| | |
|---|---|
| $R^1$-A-Cy-$Z^1$-Cy-$R^2$ | If1 |
| $R^1$-A-Ph-$Z^2$-Ph-$R^2$ | If2 |
| $R^1$-A-Ph-$Z^1$-Cy-$R^2$ | If3 |
| $R^1$-A-Cy-$Z^1$-Ph-$R^2$ | If4 |

Of these, those of the part formulae If1, If2 and If3, in particular those in which $Z^1$ is —CO—O—, —O—CO— or —CH$_2$CH$_2$—, in particular —CO—O—, are particularly preferred.

The preferred compounds of the formula Ig comprise those of the part formulae Ig1 to Ig3:

| | |
|---|---|
| $R^1$-A-$Z^1$-Cy-Cy-$R^2$ | Ig1 |
| $R^1$-A-$Z^1$-Ph-Cy-$R^2$ | Ig2 |
| $R^1$-A-$Z^1$-Ph-Ph-$R^2$ | Ig3 |

Of these, those in which $Z^1$ is —O—CO—, —CO—O— or —CH$_2$CH$_2$— are particularly preferred.

The preferred compounds of the formula Ij comprise those of the part formulae Ij1 and Ij2:

| | |
|---|---|
| $R^1$-Cy-A-Ph-Ph-$R^3$ | Ij1 |
| $R^1$-Cy-A-Ph-Cy-$R^3$ | Ij2 |

The preferred compounds of the formula Ik comprise those of the part formulae Ik1 and Ik2:

| | |
|---|---|
| $R^1$-A-Ph-Ph-Cy-$R^3$ | Ik1 |
| $R^1$-A-Ph-Cy-Cy-$R^3$ | Ik2 |

In the compounds of the abovementioned and following formulae, $R^1$, $R^2$ and $R^3$ are preferably alkyl, furthermore alkoxy or another oxaalkyl group.

Preference is further given to compounds of the abovementioned and following formulae in which one of the radical [sic] $R^1$, $R^2$ and $R^3$ is —CO—alkyl, —O—CO—alkyl, —CO—O—alkyl or CN and the other is alkyl.

In the preferred compounds of the abovementioned and following formulae, the alkyl radicals in which a CH₂ group (alkoxy or oxaalkyl) can also be replaced by an 0 atom can be straight-chain or branched. Preferably they are straight-chain, have 2, 3, 4, 5, 6 or 7 C atoms and accordingly preferably are ethyl, propyl, butyl, pentyl, hexyl, heptyl, ethoxy, propoxy, butoxy, pentoxy, hexoxy, heptoxy, 2-oxapropyl (=2-methoxymethyl), 2-(=ethoxymethyl) or 3-oxabutyl (=2-methoxypentyl), 2-, 3- or 4-oxapentyl, 2-, 3-, 4- or 5-oxahexyl, 2-, 3-, 4-, 5- or 6-oxaheptyl, and furthermore methyl, octyl, nonyl, methoxy, octoxy or nonoxy.

A², A³ and A⁴ are preferably Cy or Ph. Z¹ and Z² are preferably single bonds, less preferably —O—CO—, —CO—O— or —CH₂CH₂— groups.

A is preferably a group selected from the formulae (A) to (G)

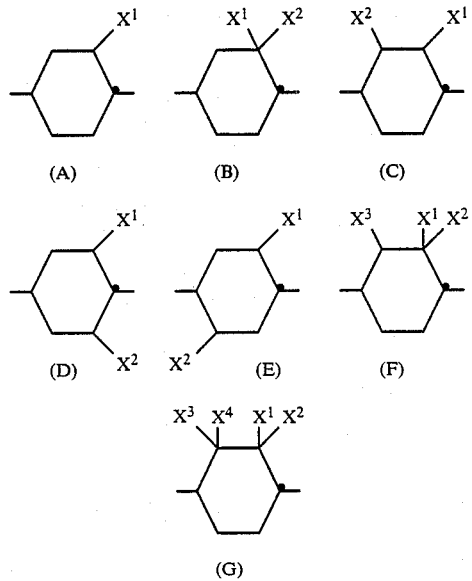

in which X¹, X², X³ and X⁴ are each, independently of one another, F, Cl, Br, CN, alkyl, alkoxy, oxaalkyl, alkanoyl, alkanoxloxy [sic] or alkoxycarbonyl each with 1 to 10 carbon atoms.

A also comprises the mirror images of the formulae (A) to (G).

The groups of the formulae (A) to (G) can have an additional axial substituent Q in the 1- or 4-position. Q is preferably F, CN or CH₃. Particular preference is given to CN.

Preferred meanings of X¹, X², X³ and X⁴ are F, Cl, CN, —CH₃, —CH₂CH₃ and —OCH₃.

Particular preference is given to the groups F, CN and CH₃, in particular CN and CH₃.

Compounds of the abovementioned and following formulae with branched wing groups R¹, R² and R³ can occasionally be of importance, by reason of better solubility in the customary liquid-crystalline base materials, but in particular for use as chiral dopants, if they are optically active. Branched groups of this kind generally contain no more than one chain branching. Such compounds are usable as components of smectic mixtures having ferroelectric properties.

Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

Of the compounds of the formula I and also Ia to It, preference is given to those in which at least one of the radicals contained therein has one of the specified preferred meanings.

Particular preference is given to compounds of the formula I containing the structural element

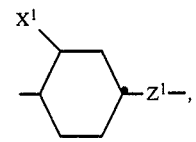

in which the cyclohexane ring may also be substituted in the 1- or 4-position. X¹ is preferably CH₃.

In the compounds of the abovementioned formulae, preference is given to those stereoisomers in which the substituents R¹-, R¹-A⁴-, R²-A²-Z¹- or R²-A²-Z¹-A⁴- are in the trans configuration in the 1- and 4-position of the ring A and occupy the equitorial position, while the optionally present additional substituent Q occupies on A an axial position in the 1- or 4-position. These are generally more stable; in many cases the cis compounds (or mixtures) can be converted into the trans compounds by treatment with a base, for example with K tert.-butylate in an inert solvent such as dimethyl sulfoxide.

The substituents X¹, X², X³ and X⁴ can occupy equatorial or axial positions in the groups of the formulae (A), (C), (D), (E) and (F). Preferably these substituents are in equatorial positions.

Those of the abovementioned formulae which contain one or more groups Dio, Dit, Pip and/or Pyr comprise in each case the two possible 2,5-(Dio, Dit, Pyr) and 1,4-position isomers (Pip).

The compounds of the formula I can be prepared by methods known per se, as described in the literature (for example in the standard works such as Houben-Weyl, Methoden der organischen Chemie [Methods of Organic Chemistry], published by Georg Thieme, Stuttgart), under reaction conditions which are known and suitable for the reactions mentioned. In carrying out these reactions, it is also possible to take advantage of variants known per se which are not specifically mentioned here.

The starting substances can if desired also be formed in situ, by not isolating them out of the reaction mixture but immediately reacting them further to the compounds of the formula I.

For instance, the compounds of the formula I can be prepared by reducing a compound which otherwise conforms to the formula 1 but in place of H atoms contains one or more reducible groups and/or C—C bonds.

Suitable reducible groups are preferably carbonyl groups, in particular keto groups, and also for example free or esterified hydroxyl groups or aromatically bonded halogen atoms. Preferred starting materials for the reduction conform to the formula I, but in place of a cyclohexane ring can contain a cyclohexene ring or cyclohexanone ring and/or in place of a —CH₂CH₂— group a —CH═CH group and/or in place of a —CH₂— group a —CO— group and/or in place of an H atom a free or functionally (for example in the form of its p-toluenesulfonate) modified OH groups [sic].

The reduction can be effected for example by catalytic hydrogenation at temperatures between 0° and about 200° and pressures between about 1 and 200 bar in an inert solvent, for example an alcohol, such as methanol, ethanol or isopropanol, an ester such as tetrahydrofuran (THF) or dioxane, an ester such as ethyl acetate, a carboxylic acid such as acetic acid or a hydrocarbon such as cyclohexane. Suitable catalysts are preferably noble metals such Pt or Pd, which can be used in the form of oxides (for example $PtO_2$, $PdO_2$), on a carrier (for example Pd on carbon, calcium carbonate or strontium carbonate) or in finely divided form.

Ketones can also be reduced to the corresponding compounds of the formula I which contain alkyl groups and/or —$CH_2CH_2$— bridges by the methods of Clemmensen (with zinc, amalgamated zinc or tin and hydrochloric acid, preferably an aqueous alcoholic solution or in heterogeneous phase with water/toluene at temperatures between about 80° and 120°) or Wolff-Kishner (with hydrazine, preferably in the presence of alkali such as KOH or NaOH in a high-boiling solvent such as diethylene glycol or triethylene glycol at temperatures between about 100° and 200°).

Reductions with complex hydrides are also possible. For example, arylsulfonyloxy groups can be reductively removed with $LiAlH_4$, in particular p-toluenesulfonyoxymethyl [sic] groups can be reduced to methyl groups, preferably in an inert solvent such as diethyl ether or THF at temperatures between about 0° and 100°. Double bonds can (even in the presence of CN groups!) be hydrogenated with $NaBH_4$ or tributyltin hydride in methanol; in this way, for example, 1-cyanocyclohexene derivatives give rise to the corresponding cyclohexane derivatives.

Compounds of the compound I are further obtainable by free radical addition of a compound of the formula $Q^1Q^2$ (for example HBr, BrCN, BrF, BrCl or $Br_2$) onto an appropriate cyclohexane derivative (which conforms to the formula I but in place of the radical A contains a 1-cyclohexene-1,4-diyl group which can carry one or two further F, Cl or Br atoms and/or CN groups.

This addition is possible for example in the presence of an inert solvent, for example a halogenated hydrocarbon such as $CH_2Cl_2$ or $CHCl_3$, at temperatures between about −10° and +150° and pressures between about 1 and 100 bar. The addition of free radical initiators or performing the reaction as a photoreaction can be favorable.

Esters of the formula I can also be obtained by esterifying appropriate carboxylic acids (or their reactive derivatives) with alcohols and phenols (or their reactive derivatives).

Suitable reactive derivatives of the carboxylic acids mentioned are in particular the acid halides, especially the chlorides and bromides, and also the anhydrides, including for example mixed anhydrides, azides or esters, in particular alkyl esters having 1–4 C atoms in the alkyl group.

Suitable reactive derivatives of the alcohols and phenols mentioned are in particular the corresponding metal alcoholates and phenolates, preferably of an alkali metal such as Na or K.

The esterification is advantageously carried out in the presence of an inert solvent. Highly suitable are in particular ethers such as diethyl ether, di-n-butyl ether, THF, dioxane or anisole, ketones such as acetone, butanone or cyclohexanone, amides such as DMF or hexamethylphosphoramide, hydrocarbons such as benzene, toluene or xylene, halogenated hydrocarbons such as carbon tetrachloride or tetrachloroethylene and sulfoxides such as methyl sulfoxide or sulfolane. Water-immiscible solvents can at the same time advantageously be used for removing by azeotropic distillation the water formed in the course of the esterification. Occasionally it is also possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is customarily between −50° and +250°, preferably between −20° and +80°. At these temperatures, the esterification reactions are generally complete after 15 minutes to 48 hours.

In detail, the reaction conditions for the esterification largely depend on the nature of the starting materials used. For instance, a free carboxylic acid is generally reacted with a free alcohol or phenol in the presence of a strong acid, for example a mineral acid such as hydrochloric acid or sulfuric acid. A preferred way of carrying out the reaction is to react an acid anhydride or in particular an acid chloride with an alcohol, preferably in a basic medium, intersecting bases being in particular alkali metal hydroxides such as sodium hydroxide or potassium hydroxide, alkali metal carbonates and hydrogencarbonates such as sodium carbonate, potassium carbonate or potassium hydrogencarbonate, alkali metal acetates such as sodium acetates or potassium acetate, alkaline earth metal hydroxides such as calcium hydroxide or organic bases such as triethylamine, pyridine, lutidine, collidine or quinoline. A further preferred embodiment of the esterification consists in first converting the alcohol or the phenol into the sodium or potassium alcoholate or phenolate, for example by treatment with ethanolic sodium hydroxide or potassium hydroxide solution, isolating the alcoholate or phenolate and suspending it together with sodium hydrogencarbonate or potassium carbonate in acetone or diethyl ether with stirring, and adding to this suspension a solution of the acid chloride or anhydride in diethyl ether, acetone or DMF, preferably at temperatures at between about −25° and +20°.

Dioxane derivatives and dithiane derivatives of the formula I are preferably prepared by reacting an appropriate aldehyde (or one of its reactive derivatives) with an appropriate 1,3-diol or an appropriate 1,3-dithiol (or one of their reactive derivatives), preferably in the presence of an inert solvent such as benzene or toluene and/or of a catalyst, for example of a strong acid such as sulfuric acid, benzenesulfonic acid or p-toluenesulfonic acid, at temperatures between 20° and about 150°, preferably between 80° and 120°. Suitable reactive derivatives of the starting materials are primarily acetals.

The said aldehydes and 1,3-diols or 1,3-dithiols and also their reactive derivatives are partly known; all can be prepared without difficulties from compounds described in the literature by standard methods of organic chemistry. For example, the aldehydes are obtainable by oxidizing appropriate alcohols or by reducing appropriate carboxylic acids or their derivatives, the diols by reducing appropriate diesters and the dithiols by reacting appropriate dihalides with NaSH.

To prepare nitriles of the formula I, appropriate acid amides, for example those in which a $CONH_2$ stands in place of the radical X, can be dehydrated. The amides are obtainable for example from appropriate esters or acid halides by reaction with ammonia. Suitable water-eliminating agents are for example inorganic acid chlorides such as $SOCl_2$, $PCl_3$, $PCl_5$, $POCl_3$, $SO_2Cl_2$, $COCl_2$, and also $P_2O_5$, $P_2S_5$, $AlCl_3$ (for example as double compounds with NaCl), aromatic sulfonic acids and sulfonyl halides. The reaction can be carried out in the presence or absence of an inert solvent at temperatures between about 0° and 150°; suitable solvents are for example bases such as pyridine or triethylamine, aromatic hydrocarbons such as benzene, toluene or xylene or amides such as DMF.

To prepare the abovementioned nitriles of the formula I it is also possible to react appropriate acid halides, preferably the chlorides, with sulfamide, preferably in an inert solvent such as tetramethylene sulfone at temperatures between about 80° and 150°, preferably at 120°. After the customary working up the nitriles can be isolated directly.

Ethers of the formula I are obtainable by etherifying appropriate hydroxy compounds, preferably appropriate phenols, the hydroxy compound being preferably first converted into a corresponding metal derivative, for example by treatment with HaH, $HaNH_2$ [sic], NaOH, KOH, $Na_2CO_3$ or $K_2CO_3$, into the corresponding alkali metal alcoholate or alkali metal phenolate. This alcoholate or phenolate can then be reacted with the corresponding alkyl halide, alkyl sulfonate or dialkyl sulfate, preferably in an inert solvent such as acetone, 1,2-dimethoxyethane, DMF or dimethyl sulfoxide or also an excess of aqueous or aqueous-alcoholic NaOH or KOH at temperatures between about 20° and 100°.

Fluorine compounds of the formula I in which A is an F-substituted 1,4-cyclohexylene group which can additionally carry further substituents are obtainable by treating the corresponding hydroxyl compounds or bromine or chlorine compounds with a fluorinating agent. Suitable fluorinating agents are all the compounds known for these replacement reactions, for example diethylaminesulfur trifluoride (J. Org. Chem. 40 (5), 574-8 (1975). The hydroxyl, bromine and chlorine compounds are obtainable for example from the corresponding cyclohexane compounds by addition of $H_2O$, HBr or HCl.

To prepare nitriles of the formula I, it is also possible to react appropriate chlorine or bromine compounds of the formula I with a cyanide, preferably with a metal cyanide such as NaCN, KCN or $Cu_2(CN)_2$, for example in the presence of pyridine in an inert solvent such as DMF or N-methylpyrrolidone at temperatures between 20° and 200°.

The liquid-crystalline phases according to the invention consist of 2 to 20, preferably 3 to 15, components, including at least one compound of the formula I. The other constituents are preferably selected from the nematic or nematogenic substances, in particular the known substances, from the classes of the azoxybenzenes, benzylideneanilines, biphenyls, terphenyls, phenyl or cyclohexyl benzoates, phenyl or cyclohexyl cyclohexane carboxylates, phenylcyclohexanes, cyclohexylbiphenyls, cyclohexylcyclo-hexanes, cyclohexylnaphthalenes, 1,4-biscyclohexylbenzenes, 4,4'-biscyclohexylbiphenyls, phenylpyrimidines, cyclohexylpyrimidines, phenylpyridazines, cyclohexylpyridazines and their N-oxides, phenyldioxanes, cyclohexyldioxanes, phenyl-1,3-dithianes, cyclohexyl-1,3-dithianes, 1,2-dephenylethanes, 1,2-dicyclohexylethanes, 1-phenyl-2-cyclohexyleth-anes, optionally halogenated stilbenes, benzyl phenyl ethers, tolanes and substituted cinnamic acids.

The most important compounds which are suitable for use as constituents of such liquid-crystalline phase can be characterized by the formula I'

$$R'—L—G—E—R''\qquad\qquad I'$$

in which L and E are each the carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene, tetrahydronaphthalene, quinazoline and tetrahydroquinazoline, G is

| | |
|---|---|
| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond,

Y is halogen, preferably chlorine or —CN, and

R' and R" are alkyl, alkoxy, alkanoyloxy, alkoxycarbonyl or alkoxycarbonyloxy having up to 18, preferably up to 8, carbon atoms, or one of these radicals can also be CN, NC, $NO_2$, $CF_3$, F, Cl or Br.

With most of these compounds, R' and R" are different from each Other, one of these radicals usually being an alkyl or alkoxy group. However, other variants of the proposed substituents are also customary. Many such substances or even mixtures thereof are commercially available. All these substances are obtainable by methods described in the literature.

The phases according to the invention contain about 0.1 to 99%, preferably 10 to 95%, of one or more compounds of the formula I, preference is further given to liquid-crystalline phases according to the invention which contain 0.1–40%, preferably 0.5–30%, of one or more compounds of the formula I.

The phases according to the invention are prepared in a conventional manner. In general, the components are dissolved in one another, preferably at elevated temperature.

By means of suitable additives the liquid-crystalline phases of the invention can be modified in such a way that they can be used in all hitherto disclosed kinds of liquid crystal display elements.

Such additives are known to the skilled worker and are exhaustively described in the literature. It is possible to add, for example, conducting salts, preferably ethyldimethyldodecylammonium 4-hexyloxybenzoate, tetrabutylammonium tetraphenylboranate or complex salts of crown ethers (cf. for example I. Haller et al., Mol. Cryst. Liq. Cryst. Volume 24, pages 249–258 (1973)) for improving the conductivity, pleochroic dyes for preparing colored guest-host systems or substances for changing the dielectric anisotrophy [sic], the viscosity and/or the orientation of the nematic phases. Such substances are described for example in German Offenlegungsschriften 2,209,127, 2,240,864, 2,321,632, 2,338,281, 2,450,088, 2,637,430, 2,853,728 and 2,902,177.

The invention is illustrated by the non-limiting examples which follow. m.p.=melting point, c.p.=clear point. Heretofore and hereinafter, percentages are by weight; all temperatures are given in degrees Celsius. "Customary working up" means: adding water, extracting with methylene chloride, separating off, drying the organic phase, evaporating to dryness and purifying the product by crystallization and/or chromatography.

EXAMPLE 1

A solution of 56 g of 2-methyl-1-(p-n-pentylphenyl)-4-n-propylcyclohexene [obtainable by reacting 2-methyl-4-propylcyclohexanone (obtainable by reacting 4-propylcyclohexanone with NaH and diethyl carbonate, methylating the resulting cyclohexanecarboxylic acid ester with methyl iodide/NaOEt/EtOH, hydrolyzing the ester and decarboxylation) with the p-n-pentylbromobenzene-based Grignard compound, subsequent hydrolysis and water elimination with p-toluenesulfonic acid/toluene] in 500 ml of THF is hydrogenated at 40° and 1 bar over 8 g of 10% Pd/C until 0.2 mol of H$_2$ has been absorbed. This is followed by filtration, evaporation and separating the resulting mixture of isomers by chromatography and crystallization. This gives r-2-methyl-t-1-(p-n-pentylphenyl)-c-4-n-propylcyclohexane and r-2-methyl-c-1-(p-n-pentylphenyl)-t-4-n-propylcyclohexane.

This method is also used to prepare:
2-methyl-1-(p-butylphenyl)-4-propylcyclohexane
2-methyl-1-(p-propylphenyl)-4-propylcyclohexane
2-methyl-1-(p-ethylphenyl)-4-propylcyclohexane
2-methyl-1-(p-methoxyphenyl)-4-propylcyclohexane
2-methyl-1-(p-ethoxyphenyl)-4-propylcyclohexane
2-methyl-1-(p-propoxyphenyl)-4-propylcyclohexane
2-methyl-1-(p-cyanophenyl)-4-propylcyclohexane 2-methyl-1-(p-heptylphenyl)-4-pentylcyclohexane
2-methyl-1-(p-pentylphenyl)-4-pentylcyclohexane
2-methyl-1-(p-butylphenyl)-4-pentylcyclohexane
2-methyl-1-(p-propylphenyl)-4-pentylcyclohexane
2-methyl-1-(p-ethylphenyl)-4-pentylcyclohexane
2-methyl-1-(p-methoxyphenyl)-4-pentylcyclohexane
2-methyl-1-(p-ethoxyphenyl)-4-pentylcyclohexane
2-methyl-1-(p-propoxyphenyl)-4-pentylcyclohexane
2-methyl-1-(p-cyanophenyl)-4-pentylcyclohexane 3-methyl-1-(p-heptylphenyl)-4-butylcyclohexane
3-methyl-1-(p-pentylphenyl)-4-butylcyclohexane
3-methyl-1-(p-butylphenyl)-4-butylcyclohexane
3-methyl-1-(p-propylphenyl)-4-butylcyclohexane
3-methyl-1-(p-ethylphenyl)-4-butylcyclohexane
3-methyl-1-(p-methoxyphenyl)-4-butylcyclohexane
3-methyl-1-(p-ethoxyphenyl)-4-butylcyclohexane
3-methyl-1-(p-propoxyphenyl)-4-butylcyclohexane
3-methyl-1-(p-cyanophenyl)-4-butylcyclohexane

EXAMPLE 2

A solution of 72 g of 2-methyl-1-(p-n-pentylphenyl)-4-(trans-4-n-propylcyclohexyl)-cyclohexane [obtainable by reacting 2-methyl-4-(trans-4-n-propylcyclohexyl)-cyclohexanone with NaH and diethyl carbonate, methylating the resulting cyclohexanecarboxylic acid ester with methyl iodide/NaOEt/EtOH, hydrolyzing the ester and decarboxylation) with the p-n-pentylbromobenzene-based Grignard compound, subsequent hydrolysis and water elimination in 500 ml of THF is hydrogenated at 40° C. and 1 bar over 8 g of 10% Pd/C until 0.2 mol of H$_2$ has been absorbed. This is followed by filtration, evaporation and separating the resulting mixture of isomers by chromatography and crystallization. This gives r-2-methyl-t-1-(p-n-phentylphenyl)-c-4-(trans-4-n-propylcyclohexyl)-cyclohexane and r-2-methyl-c-1-(p-n-pentylphenyl)-t-4-(trans-4-n-propylcyclohexyl)-cyclo-hexane.

The same method is also used to prepare
2-methyl-1-(p-butylphenyl)-4-(trans-4-propylcyclohexyl)-cyclohexane
2-methyl-1-(p-propylphenyl)-4-(trans-4-propylcyclohexyl)-cyclohexane
2-methyl-1-(p-ethylphenyl)-4-(trans-4-propylcyclohexyl)-cyclohexane
2-methyl-1-(p-methoxyphenyl)-4-(trans-4-propylcyclohexyl)-cyclohexane
2-methyl-1-(p-ethoxyphenyl)-4-(trans-4-propylcyclohexyl)-cyclohexane
2-methyl-1-(p-propoxyphenyl)-4-(trans-4-propylcyclohexyl)-cyclohexane
2-methyl-1-(p-cyanophenyl)-4-(trans-4-propylcyclohexyl)-cyclohexane 2-methyl-1-(p-ethylphenyl)-4-(trans-4-butylcyclohexyl)-cyclohexane
2-methyl-1-(p-propylphenyl)-4-(trans-4-butylcyclohexyl)-cyclohexane
2-methyl-1-(p-butylphenyl)-4-(trans-4-butylcyclohexyl)-cyclohexane
2-methyl-1-(p-pentylphenyl)-4-(trans-4-butylcyclohexyl)-cyclohexane
2-methyl-1-(p-methoxyphenyl)-4-(trans-4-butylcyclohexyl)-cyclohexane
2-methyl-1-(p-ethoxyphenyl)-4-(trans-4-butylcyclohexyl)-cyclohexane
2-methyl-1-(p-propoxyphenyl)-4-(trans-4-butylcyclohexyl)-cyclohexane
2-methyl-1-(p-butoxyphenyl)-4-(trans-4-butylcyclohexyl)-cyclohexane
2-methyl-1-(p-cyanophenyl)-4-(trans-4-butylcyclohexyl)-cyclohexane 2-methyl-1-(p-ethylphenyl)-4-(trans-4-pentylcyclohexyl)-cyclohexane
2-methyl-1-(p-propylphenyl)-4-(trans-4-pentylcyclohexyl)-cyclohexane
2-methyl-1-(p-butylphenyl)-4-(trans-4-pentylcyclohexyl)-cyclohexane
2-methyl-1-(p-pentylphenyl)-4-(trans-4-pentylcyclohexyl)-cyclohexane
2-methyl-1-(p-methoxyphenyl)-4-(trans-4-pentylcyclohexyl)-cyclohexane
2-methyl-1-(p-ethoxyphenyl)-4-(trans-4-pentylcyclohexyl)-cyclohexane
2-methyl-1-(p-propoxyphenyl)-4-(trans-4-pentylcyclohexyl)-cyclohexane
2-methyl-1-(p-butoxyphenyl)-4-(trans-4-pentylcyclohexyl)-cyclohexane
2-methyl-1-(p-cyanophenyl)-4-(trans-4-pentylcyclohexyl)-cyclohexane

EXAMPLE 3

A mixture of 23.8 g of 4-(trans-4-n-propylcyclohexyl)-2-methylcyclohexanol [obtainable by reducing the corresponding ketone (Example 2) with lithium aluminum hydride], 2.4 g of NaH and 150 ml of dimethoxyethane is heated under an N$_2$ atmosphere to about 16° C., and 16 g of diethyl sulfate are then added with vigorous stirring. Stirring is continued at the stated temperature for 12 hours, and after cooling down the reaction mixture is then hydrolyzed with aqueous THF. Customary working up gives r-2-methyl-t-1-ethoxy-c-4-(trans-4-n-propylcyclohexyl)-cyclohexane and r-2-methyl-c-1-ethoxy-t-4-(trans-4-n-propylcyclohexyl)-cyclohexane.

The same method is used to prepare:
2-methyl-1-methoxy-4-(trans-4-propylcyclohexyl)-cyclohexane
2-methyl-1-propoxy-4-(trans-4-propylcyclohexyl)-cyclohexane
2-methyl-1-butoxy-4-(trans-4-propylcyclohexyl)-cyclohexane 2-methyl-1-methoxy-4-(trans-4-butylcyclohexyl)-cyclohexane
2-methyl-1-ethoxy-4-(trans-4-butylcyclohexyl)-cyclohexane
2-methyl-1-propoxy-4-(trans-4-butylcyclohexyl)-cyclohexane
2-methyl-1-butoxy-4-(trans-4-butylcyclohexyl)-cyclohexane 2-methyl-1-methoxy-4-(trans-4-pentylcyclohexyl)-cyclohexane
2-methyl-1-ethoxy-4-(trans-4-pentylcyclohexyl)-cyclohexane
2-methyl-1-propoxy-4-(trans-4-pentylcyclohexyl)-cyclohexane
2-methyl-1-butoxy-4-(trans-4-pentylcyclohexyl)-cyclohexane 2-ethyl-1-methoxy-4-(trans-4-pentylcyclohexyl)-cyclohexane
2-ethyl-1-ethoxy-4-(trans-4-pentylcyclohexyl)-cyclohexane
2-ethyl-1-propoxy-4-(trans-4-pentylcyclohexyl)-cyclohexane
2-ethyl-1-butoxy-4-(trans-4-pentylcyclohexyl)-cyclohexane

EXAMPLE 4

A solution of 22 g of p-(2-methyl-4-n-propylcyclohexyl)benzamide [obtainable from the acid chloride with NH$_3$; the corresponding acid being obtainable by reacting phenylmagnesium bromide with 2-methyl-4-n-propylcyclohexanone (Example 1), elimination of water, hydrogenation of the resulting double bond, Friedel-Crafts acylation with acetyl chloride and subsequent haloform reaction] in 500 ml of DMF has added to it dropwise with stirring at 50° 65 g of POCl$_3$. After further stirring for one hour the batch is poured onto ice and is worked up as customary to give p-(2-methyl-4-n-propylcyclohexyl)-benzonitrile.

The same method is used to prepare:
p-(2-methyl-4-ethylcyclohexyl)-benzonitrile
p-(2-methyl-4-butylcyclohexyl)-benzonitrile
p-(2-methyl-4-pentylcyclohexyl)-benzonitrile
p-(2-methyl-4-hexylcyclohexyl)-benzonitrile
p-(2-methyl-4-heptylcyclohexyl)-benzonitrile
p-(2-methyl-4-octylcyclohexyl)-benzonitrile p-(3-methyl-4-ethylcyclohexyl)-benzonitrile
p-(3-methyl-4-propylcyclohexyl)-benzonitrile
p-(3-methyl-4-butylcyclohexyl)-benzonitrile
p-(3-methyl-4-pentylcyclohexyl)-benzonitrile
p-(3-methyl-4-hexylcyclohexyl)-benzonitrile
p-(3-methyl-4-heptylcyclohexyl)-benzonitrile
p-(3-methyl-4-octylcyclohexyl)-benzonitrile

EXAMPLE 6

20 g of p-(2-methyl-4-n-propylcyclohexyl)-benzoic acid (Examaple 5) is boiled for 1 hour with 24 g of SOCl$_2$, the mixture is evaporated to dryness, the resulting crude acid chloride is dissolved in 150 ml of toluene, to which are added 8 ml of pyridine and 13.2 g of ethylphenol, and the mixture is boiled for 2 hours. Cooling down and customary working up give p-ethylphenyl p-(2-methyl-4-n-propylcyclohexyl)-benzoate.

The same method is used to prepare:
p-propylphenyl p-(2-methyl-4-propylcyclohexyl)-benzoate
p-butylphenyl p-(2-methyl-4-propylcyclohexyl)-benzoate
p-pentylphenyl p-(2-methyl-4-propylcyclohexyl)-benzoate
p-methoxyphenyl p-(2-methyl-4-propylcyclohexyl)-benzoate
p-ethoxyphenyl p-(2-methyl-4-propylcyclohexyl)-benzoate
p-propoxyphenyl p-(2-methyl-4-propylcyclohexyl)-benzoate
p-butoxyphenyl p-(2-methyl-4-propylcyclohexyl)-benzoate
p-cyanophenyl p-(2-methyl-4-propylcyclohexyl)-benzoate p-propylphenyl p-(2-methyl-4-butylcyclohexyl)-benzoate
p-butylphenyl p-(2-methyl-4-butylcyclohexyl)-benzoate
p-pentylphenyl p-(2-methyl-4-butylcyclohexyl)-benzoate
p-methoxyphenyl p-(2-methyl-4-butylcyclohexyl)-benzoate
p-ethoxyphenyl p-(2-methyl-4-butylcyclohexyl)-benzoate
p-propoxyphenyl p-(2-methyl-4-butylcyclohexyl)-benzoate
p-butoxyphenyl p-(2-methyl-4-butylcyclohexyl)-benzoate
p-cyanophenyl p-(2-methyl-4-butylcyclohexyl)-benzoate p-propylphenyl p-(2-methyl-4-pentylcyclohexyl)-benzoate
p-butylphenyl p-(2-methyl-4-pentylcyclohexyl)-benzoate
p-pentylphenyl p-(2-methyl-4-pentylcyclohexyl)-benzoate
p-methoxyphenyl p-(2-methyl-4-pentylcyclohexyl)-benzoate
p-ethoxyphenyl p-(2-methyl-4-pentylcyclohexyl)-benzoate
p-propoxyphenyl p-(2-methyl-4-pentylcyclohexyl)-benzoate
p-butoxyphenyl p-(2-methyl-4-pentylcyclohexyl)-benzoate
p-cyanophenyl p-(2-methyl-4-pentylcyclohexyl)-benzoate
trans-4-ethylcyclohexyl p-(2-methyl-4-pentylcyclohexyl)-benzoate
trans-4-propylcyclohexyl p-(2-methyl-4-pentylcyclohexyl)-benzoate
trans-4-butylcyclohexyl p-(2-methyl-4-pentylcyclohexyl)-benzoate
trans-4-pentylcyclohexyl p-(2-methyl-4-pentylcyclohexyl)-benzoate trans-4-ethylcyclohexyl p-(2-methyl-4-butylcyclohexyl)-benzoate
trans-4-propylcyclohexyl p-(2-methyl-4-butylcyclohexyl)-benzoate
trans-4-butylcyclohexyl p-(2-methyl-4-butylcyclohexyl)-benzoate
trans-4-pentylcyclohexyl p-(2-methyl-4-butylcyclohexyl)-benzoate
trans-4-ethylcyclohexyl p-(2-methyl-4-propylcyclohexyl)-benzoate
trans-4-propylcyclohexyl p-(2-methyl-4-propylcyclohexyl)-benzoate
trans-4-butylcyclohexyl p-(2-methyl-4-propylcyclohexyl)-benzoate
trans-4-pentylcyclohexyl p-(2-methyl-4-propylcyclohexyl)-benzoate

EXAMPLE 7

177.5 g of trans-4-(4-n-propyl-2-methylcyclohexyl)-cyclohexanecarboxamide [obtainable by standard methods from the corresponding carboxylic acid, which in turn is obtained by haloform degradation from Example 11 and subsequent hydrogenation] are suspended in 150 ml of $CH_2Cl_2$, and 1 ml of DMF is added. 7.3 ml or thionyl chloride are added dropwise at the boil, and the batch is stirred for 4 hours. After cooling down to room temperature the reaction mixture is discharged onto ice-water and worked up as customary to give trans-4-(4-n-propyl-2-methylcyclohexyl)-cyclohexanecarbonitrile.

The same method is used to prepare:
trans-4-(trans-4-ethyl-2-methylcyclohexyl)-cyclohexanecarbonitrile
trans-4-(trans-4-butyl-2-methylcyclohexyl)-cyclohexanecarbonitrile
trans-4-(trans-4-pentyl-2-methylcyclohexyl)-cyclohexanecarbonitrile
trans-4-(trans-4-heptyl-2-methylcyclohexyl)-cyclohexanecarbonitrile

EXAMPLE 8

A mixture of 26.6 g of trans-4-(4-n-propyl-2-methylcyclohexyl)-cyclohexanecarboxylic acid and 14.2 g of trans-4-n-propylcyclohexanol is heated in toluene together with a catalytic amount of p-toluenesulfonic acid at the boil under a water separator for 2 hours. After cooling down the toluene solution is washed in $Na_2CO_3$ solution and worked up as customary to give trans-4-n-propylcyclohexyl trans-4-(trans-4-n-propyl-2-methylcyclohexyl)-cyclohexanecarboxylate.

The same method is used to prepare:
trans-4-ethylcyclohexyl trans-4-(trans-4-propyl-2-methylcyclohexyl)-cyclohexanecarboxylate
trans-4-butylcyclohexyl trans-4-(trans-4-propyl-2-methylcyclohexyl)-cyclohexanecarboxylate
trans-4-pentylcyclohexyl trans-4-(trans-4-propyl-2-methylcyclohexyl)-cyclohexanecarboxylate
trans-4-ethylcyclohexyl trans-4-(trans-4-ethyl-2-methylcyclohexyl)-cyclohexanecarboxylate
trans-4-propylcyclohexyl trans-4-(trans-4-ethyl-2-methylcyclohexyl)-cyclohexanecarboxylate
trans-4-butylcyclohexyl trans-4-(trans-4-ethyl-2-methylcyclohexyl)-cyclohexanecarboxylate
trans-4-pentylcyclohexyl trans-4-(trans-4-ethyl-2-methylcyclohexyl)-cyclohexanecarboxylate
trans-4-ethylcyclohexyl trans-4-(trans-4-butyl-2-methylcyclohexyl)-cyclohexanecarboxylate
trans-4-propylcyclohexyl trans-4-(trans-4-butyl-2-methylcyclohexyl)-cyclohexanecarboxylate
trans-4-butylcyclohexyl trans-4-(trans-4-butyl-2-methylcyclohexyl)-cyclohexanecarboxylate
trans-4-pentylcyclohexyl trans-4-(trans-4-butyl-2-methylcyclohexyl)-cyclohexanecarboxylate
trans-4-ethylcyclohexyl trans-4-(trans-4-pentyl-2-methylcyclohexyl)-cyclohexanecarboxylate
trans-4-propylcyclohexyl trans-4-(trans-4-pentyl-2-methylcyclohexyl)-cyclohexanecarboxylate
trans-4-butylcyclohexyl trans-4-(trans-4-pentyl-2-methylcyclohexyl)-cyclohexanecarboxylate
trans-4-pentylcyclohexyl trans-4-(trans-4-pentyl-2-methylcyclohexyl)-cyclohexanecarboxylate
trans-4-ethylcyclohexyl trans-4-(trans-4-heptyl-2-methylcyclohexyl)-cyclohexanecarboxylate
trans-4-propylcyclohexyl trans-4-(trans-4-heptyl-2-methylcyclohexyl)-cyclohexanecarboxylate
trans-4-butylcyclohexyl trans-4-(trans-4-heptyl-2-methylcyclohexyl)-cyclohexanecarboxylate
trans-4-pentylcyclohexyl trans-4-(trans-4-heptyl-2-methylcyclohexyl)-cyclohexanecarboxylate

EXAMPLE 9

A solution of 108.7 g of trans-4-(4-propyl-2-methylcyclohexyl)-cyclohexanecarbonitrile (Example 7) in 600 ml of toluene is added in an $N_2$ atmosphere to a Grignard solution of 10.7 g of Mg chips and 66.4 g of 1-bromopentane in 500 ml of ether. The ether is distilled off of the reaction mixture, and the reaction mixture is then refluxed for 8 hours. After cooling down the batch is hydrolyzed with half-concentrated HCl and is worked up as customary to give trans-4-(trans-4-n-propyl-2-methylcyclohexyl)-cyclohexyl n-pentyl ketone.

The same method is used to prepare:
4-(4-propyl-2-methylcyclohexyl)-cyclohexyl methyl ketone
4-(4-propyl-2-methylcyclohexyl)-cyclohexyl ethyl ketone
4-(4-propyl-2-methylcyclohexyl)-cyclohexyl propyl ketone
4-(4-propylr2-methylcyclohexyl)-cyclohexyl butyl ketone
4-(4-ethyl-2-methylcyclohexyl)-cyclohexyl methyl ketone
4-(4-ethyl-2-methylcyclohexyl)-cyclohexyl ethyl ketone
4-(4-ethyl-2-methylcyclohexyl)-cyclohexyl propyl ketone
4-(4-ethyl-2-methylcyclohexyl)-cyclohexyl butyl ketone
4-(4-butyl-2-methylcyclohexyl)-cyclohexyl methyl ketone
4-(4-butyl-2-methylcyclohexyl)-cyclohexyl ethyl ketone
4-(4-butyl-2-methylcyclohexyl)-cyclohexyl propyl ketone
4-(4-butyl-2-methylcyclohexyl)-cyclohexyl butyl ketone
4-(4-pentyl-2-methylcyclohexyl)-cyclohexyl methyl ketone
4-(4-pentyl-2-methylcyclohexyl)-cyclohexyl ethyl ketone
4-(4-pentyl-2-methylcyclohexyl)-cyclohexyl propyl ketone 4-(4-pentyl-2-methylcyclohexyl)-cyclohexyl butyl ketone

EXAMPLE 10

A mixture of 32 g of ketone (Example 9), 30 ml of hydrazine hydrate, 53 g of KOH and 300 ml of diglycol is heated with stirring to the boil and the volatile constituents are distilled out of the reaction mixture until a temperature of about 200° C. is reached in the flask and the hydrazone has decomposed. The reaction mixture is then poured onto water and is worked up as customary to give trans-4-(trans-4-n-propyl-2-methylcyclohexyl)-1-n-hexylcyclohexane.

The same method is used to prepare:
4-(4-propyl-2-methylcyclohexyl)-1-ethylcyclohexane
4-(4-propyl-2-methylcyclohexyl)-1-propylcyclohexane
4-(4-propyl-2-methylcyclohexyl)-1-butylcyclohexane
4-(4-propyl-2-methylcyclohexyl)-1-pentylcyclohexane 4-(4-butyl-2-methylcyclohexyl)-1-ethylcyclohexane
4-(4-butyl-2-methylcyclohexyl)-1-propylcyclohexane
4-(4-butyl-2-methylcyclohexyl)-1-butylcyclohexane
4-(4-butyl-2-methylcyclohexyl)-1-pentylcyclohexane 4-(4-pentyl-2-methylcyclohexyl)-1-ethylcyclohexane
4-(4-pentyl-2-methylcyclohexyl)-1-propylcyclohexane
4-(4-pentyl-2-methylcyclohexyl)-1-butylcyclohexane
4-(4-pentyl-2-methylcyclohexyl)-1-pentylcyclohexane

EXAMPLE 11

In the absence of water, a vigorously stirred suspension of 160 g of AlCl$_3$ in 400 ml of 1,2-dichloroethane has added to it, dropwise, 82 g of acetyl chloride while subjected to ice-cooling, followed at 20° C. by 214 g of 4-propyl-2-methylcyclohexylbenzene (obtainable from 3-propyl-2-methylcyclohexanone and bromobenzene by Grignard reaction, subsequent water elimination and hydrogenation). The reaction mixture is then stirred for a further hour and left to stand overnight. To decompose the ketone/aluminum chloride complex, the reaction mixture is poured onto about 500 ml of ice, to which concentrated hydrochloric acid is then added. The organic layer is separated off and worked up as customary to give 4-(4-propyl-2-methylcyclohexyl)-acetophenone.

The same method is used to prepare:
4-(4-ethyl-2-methylcyclohexyl)-acetophenone
4-(4-butyl-2-methylcyclohexyl)-acetophenone
4-(4-pentyl-2-methylcyclohexyl)-acetophenone
4-(4-heptyl-2-methylcyclohexyl)-acetophenone

EXAMPLE 12

A mixture of 23.2 g of 4-(4-propyl-2-methylcyclohexyl)phenol [obtainable from 4-propyl-2-methylcyclohexylbenzene (obtainable by Grignard reaction of bromobenzene with 4-n-propyl-2-methylcyclohexanone, subsequent water elimination and hydrogenation of the double bond) by nitration, reduction of the nitro group to the amine and diazotization with subsequent boiling with phenol], 6.9 g of K$_2$CO$_3$, 19 g of butyl iodide and 200 ml of DMF is heated with stirring at 80° C. for 16 hours and then cooled down and worked up as customary to give r-1-p-butoxyphenyl-2-methyl-trans-4-n-propylcyclohexane.

The same method is used to prepare:
1-p-methoxyphenyl-2-methyl-4-propylcyclohexane
1-p-ethoxyphenyl-2-methyl-4-propylcyclohexane
1-p-propoxyphenyl-2-methyl-4-propylcyclohexane 1-p-methoxyphenyl-2-methyl-4-ethylcyclohexane
1-p-ethoxyphenyl-2-methyl-4-ethylcyclohexane
1-p-propoxyphenyl-2-methyl-4-ethylcyclohexane
1-p-butoxyphenyl-2-methyl-4-ethylcyclohexane 1-p-methoxyphenyl-2-methyl-4-butylcyclohexane
1-p-ethoxyphenyl-2-methyl-4-butylcyclohexane
1-p-propoxyphenyl-2-methyl-4-butylcyclohexane
1-p-butoxyphenyl-2-methyl-4-butylcyclohexane 1-p-methoxyphenyl-2-methyl-4-pentylcyclohexane
1-p-ethoxyphenyl-2-methyl-4-pentylcyclohexane
1-p-propoxyphenyl-2-methyl-4-pentylcyclohexane
1-p-butoxyphenyl-2-methyl-4-pentylcyclohexane

EXAMPLE 13

A mixture of 23.8 g of 4-trans-(4-n-propyl-2-methylcyclohexyl)-cyclohexanol (prepared from the phenol from Example 12 by hydrogenation), 2.4 g of NaH and 150 ml of dimethoxyethane is heated under an N$_2$ atmosphere to about 60° C. 14 g of dimethyl sulfate were then added dropwise with vigorous stirring. The reaction mixture is stirred at 60° C. for 12 hours and is then worked up as customary to give trans-4-(trans-4-n-propyl-2-methylcyclohexyl)-1-methoxycyclohexane.

The same method is used to prepare:
4-(4-propyl-2-methylcyclohexyl)-1-ethoxycyclohexane
4-(4-propyl-2-methylcyclohexyl)-1-propoxycyclohexane
4-(4-propyl-2-methylcyclohexyl)-1-butoxycyclohexane 4-(4-butyl-2-methylcyclohexyl)-1-methoxycyclohexane
4-(4-butyl-2-methylcyclohexyl)-1-ethoxycyclohexane
4-(4-butyl-2-methylcyclohexyl)-1-propoycyclohexane
4-(4-butyl-2-methylcyclohexyl-1-butoxycyclohexane 4-(4-pentyl-2-methylcyclohexyl)-1-methoxycyclohexane
4-(4-pentyl-2-methylcyclohexyl)-1-ethoxycyclohexane
4-(4-pentyl-2-methylcyclohexyl)-1-propoxycyclohexane
4-(4-pentyl-2-methylcyclohexyl)-1-butoxycyclohexane

EXAMPLE 14

A solution of 72 g of 1-(p-pentylphenyl)-4-trans-4-n-propyl-2-methylcyclohexyl)-cyclohex-1-ene (obtainable from 4-trans-4-(trans-n-propyl- 2-methylcyclohexyl)-cyclohexanol by oxidation to the ketone and a Grignard reaction with 4-pentylbromobenzene and subsequent water elimination) in 500 ml of THF is hydrogenated over 8 g of 10% strength Pd/C at 40° C. and 1 bar until 0.2 mol of H$_2$ has been absorbed. The reaction is then filtered, the filtrate is evaporated to dryness, and the resulting mixture of isomers is separated by chromatography and crystallization to give trans-1-p-n-pentylphenyl-4-(trans-4-n-propyl-2-methylcyclohexyl)-cyclohexane.

The same method is used to prepare:
1-p-butylphenyl-4-(4-propyl-2-methylcyclohexyl)-cyclohexane
1-p-propylphenyl-4-(4-propyl-2-methylcyclohexyl)-cyclohexane
1-p-ethylphenyl-4-(4-propyl-2-methylcyclohexyl)-cyclohexane
1-p-methoxyphenyl-4-(4-propyl-2-methylcyclohexyl)-cyclohexane 1-p-ethoxyphenyl-4-(4-propyl-2-methylcyclohexyl)-cyclohexane
1-p-propoxyphenyl-4-(4-propyl-2-methylcyclohexyl)-cyclohexane
1-p-butoxyphenyl-4-(4-propyl-2-methylcyclohexyl)-cyclohexane
1-p-cyanophenyl-4-(4-propyl-2-methylcyclohexyl)-cyclohexane 1-p-butylphenyl-4-(4-ethyl-2-methylcyclohexyl)-cyclohexane
1-p-propylphenyl-4-(4-ethyl-2-methylcyclohexyl)-cyclohexane
1-p-ethylphenyl-4-(4-ethyl-2-methylcyclohexyl)-cyclohexane
1-p-methoxyphenyl-4-(4-ethyl-2-methylcyclohexyl)-cyclohexane
1-p-ethoxyphenyl-4-(4-ethyl-2-methylcyclohexyl)-cyclohexane
1-p-propoxyphenyl-4-(4-ethyl-2-methylcyclohexyl)-cyclohexane
1-p-butoxyphenyl-4-(4-ethyl-2-methylcyclohexyl)-cyclohexane
1-p-cyanophenyl-4-(4-ethyl-2-methylcyclohexyl)-cyclohexane 1-p-butylphenol-4-(4-butyl-2-methylcyclohexyl)-cyclohexane
1-p-propylphenyl-4-(4-butyl-2-methylcyclohexyl)-cyclohexane
1-p-ethylphenyl-4-(4-butyl-2-methylcyclohexyl)-cyclohexane
1-p-methoxyphenyl-4-(4-butyl-2-methylcyclohexyl)-cyclohexane
1-p-ethoxyphenyl-4-(4-butyl-2-methylcyclohexyl)-cyclohexane
1-p-propoxyphenyl-4-(4-butyl-2-methylcyclohexyl)-cyclohexane
1-butoxyphenyl-4-(4-butyl-2-methylcyclohexyl)-cyclohexane
1-p-cyanophenyl-4-(4-butyl-2-methylcyclohexyl)-cyclohexane 1-p-butylphenyl-4-(4-pentyl-2-methylcyclohexy)-cyclohexane
1-p-propylphenyl-4-(4-pentyl-2-methylcyclohexyl)-cyclohexane
1-p-ethylphenyl-4-(4-pentyl-2-methylcyclohexyl)-cyclohexane
1-p-methoxyphenyl-4-(4-pentyl-2-methylcyclohexyl)-cyclohexane
1-p-ethoxyphenyl-4-(4-pentyl-2-methylcyclohexyl)-cyclohexane
1-p-propoxyphenyl-4-(4-pentyl-2-methylcyclohexyl)-cyclohexane
1-p-butoxyphenyl-4-(4-pentyl-2-methylcyclohexyl)-cyclohexane
1-p-cyanophenyl-4-(4-pentyl-2-methylcyclohexyl)-cyclohexane

EXAMPLE 15

A mixture of 43 g of 4-pentyl-4'-(trans-4-n-propyl-2-methylcyclohexylacetyl)-biphenyl [obtainable from trans-4-n-propyl-2-methylcyclohexylacetyl chloride by Friedel-Crafts acrylation of 4-pentylbiphenyl. trans-4-n-Propyl-2-methylcyclohexylacetic acid is obtained from 4-propyl-2-methylbenzoic acid by catalytic hydrogenation to give 4-propyl-2-methylcyclohexanecarboxylic acid. The subsequent isomerization by boiling with thionyl chloride and the reduction with LiAlH$_4$ gives trans-4-n-propyl-2-methylcyclohexylmethanol, the tosylate of which is reacted with NaCN to give trans-4-n-propyl-2-methylcyclohexylacetonitrile. Hydrolysis of the nitrile gives the desired carboxylic acid], 20 ml of 80% strength hydrazine hydrate and 20 g of KOH is refluxed for 2 hours in 240 ml of diethylene glycol. The reflux condenser is then replaced by a distillation attachment, and the temperature is gradually raised to 195°–200° C. and maintained there for 6 hours. A mixture of hydrazine and water distils over. After cooling down, the mixture is diluted with 300 ml of water acidified and extracted with toluene. The organic phase is repeatedly washed with water and the solvent is then removed in vacuo. The residue is purified by chromatography and crystallization to give 1-(trans-4-n-propyl-2-methylcyclohexyl)-2-(4'-n-pentylbiphenyl-4-yl)-ethane.

The same method is used to prepare:
1-(4-propyl-2-methylcyclohexyl)-2-(4'-butylbiphenyl-4-yl)-ethane
1-(4-propyl-2-methylcyclohexyl)-2-(4'-propylbiphenyl-4-yl)-ethane
1-(4-propyl-2-methylcyclohexyl)-2-(4'- ethylbiphenyl-4-yl)-ethane
1-(4-propyl-2-methylcyclohexyl)-2-(4'-methoxybiphenyl-4-yl)-ethane
1-(4-propyl-2-methylcyclohexyl)-2-(4'-ethoxybiphenyl-4-yl)-ethane
1-(4-propyl-2-methylcyclophexyl)-2-(4'-butoxybiphenyl-4-yl)-ethane
1-(4-propyl-2-methylcyclohexyl)-2-(4'-cyanobiphenyl-4-yl)-ethane 1-(4-ethyl-2-methylcyclohexyl)-2-(4'-butylbiphenyl-4-yl)-ethane
1-(4-ethyl-2-methylcyclohexyl)-2-(4'-propylbiphenyl-4-yl)-ethane
1-(4-ethyl-2-methylcyclohexyl)-2-(4'-ethylbiphenyl-4-yl)-ethane
1-(4-ethyl-2-methylcyclohexyl)-2-(4'-methoxybiphenyl-4-yl)-ethane
1-(4-ethyl-2-methylcyclohexyl)-2-(4'-ethoxybiphenyl-4-yl)-ethane
1-(4-ethyl-2-methylcyclohexyl)-2-(4'-butoxybiphenyl-4-yl)-ethane
1-(4-ethyl-2-methylcyclohexyl)-2-(4'-cyanobiphenyl-4-yl)-ethane 1-(4-butyl-2-methylcyclohexyl)-2-(4'-butylbiphenyl-4-yl)-ethane
1-(4-butyl-2-methylcyclohexyl)-2-(4'-propylbiphenyl-4-yl)-ethane
1-(4-butyl-2-methylcyclohexyl)-2-(4'-ethylbiphenyl-4-yl)-ethane
1-(4-butyl-2-methylcyclohexyl)-2-(4'-methoxybiphenyl-4-yl)-ethane
1-(4-butyl-2-methylcyclohexyl)-2-(4'-ethoxybiphenyl-4-yl)-ethane
1-(4-butyl-2-methylcyclohexyl)-2-(4'-butoxybiphenyl-4-yl)-ethane
1-(4-butyl-2-methylcyclohexyl)-2-(4'-cyanobiphenyl-4-yl)-ethane 1-(4-pentyl-2-methylcyclohexyl)-2-(4'-butylbiphenyl-4-yl)-ethane 1-(4-pentyl-2-methylcyclohexyl)-2-(4'-propylbiphenyl-4-yl)-ethane
1-(4-pentyl-2-methylcyclohexyl)-2-(4'-ethylbiphenyl-4-yl)-ethane
1-(4-pentyl-2-methylcyclohexyl)-2-(4'-methoxybiphenyl-4-yl)-ethane
1-(4-pentyl-2-methylcyclohexyl)-2-(4'-ethoxybiphenyl-4-yl)-ethane
1-(4-pentyl-2-methylcyclohexyl)-2-(4'-butoxybiphenyl-4-yl)-ethane
1-(4-pentyl-2-methylcyclohexyl)-2-(4'-cyanobiphenyl-4-yl)-ethane

EXAMPLE 16

A solution of 41 g of 4-pentyl-2-fluoro-4'-(trans-4-n-propyl-2-methylcyclohexylacetyl)-biphenyl [obtainable from trans-4-propyl-2-methylacetyl chloride by Friedel-Crafts acylation of 2-fluoro-4-pentylbiphenyl] in 200 ml of THF is hydrogenated at 50° C. under 3 bar of pressure in the presence of 12 g of Pd/C. After 0.2 mol of $H_2O$ has been absorbed, the hydrogenation is discontinued, the reaction mixture is filtered and the solvent is then removed in vacuo. The residue is purified by chromatography and crystallization to give 1-(trans-4-n-propyl-2-methylcyclohexyl)-2-(4'-n-pentyl-2'-fluorobiphenyl-4-yl)-ethane.

The same method is used to prepare:
1-(4-propyl-2-methylcyclohexyl)-2-(4'-butyl-2'-fluorobiphenyl-4-yl)-ethane
1-(4-propyl-2-methylcyclohexyl)-2-(4'-propyl-2'-fluorobiphenyl-4-yl)-ethane
1-(4-propyl-2-methylcyclohexyl)-2-(4'-ethyl-2'-fluorobiphenyl-4-yl)-ethane
1-(4-propyl-2-methylcyclohexyl)-2-(4'-methyl-2'-fluorobiphenyl-4-yl)-ethane

EXAMPLE 17

A mixture of 28.4 g of 1-(p-pentylphenyl)-2-oxo-trans-4-n-propylcyclohexane [obtainable from 1-(p-pentylphenyl)-4-propylcyclohexene by hydroboronation, cleavage of the boron compound with alkaline $H_2O_2$ and subsequent oxidation of the alcohol with pyridinium chlorochromate to give the ketone] and 13.3 g of DAST (diethylaminosulfur trifluoride) is gradually heated to 80° C. and stirred at that temperature for 1 hour. After cooling the mixture is poured onto ice-water and then extracted with methylene chloride. After drying of the organic phase, the solvent is drawn off and the residue is purified by chromatography to give r-1-(p-n-pentylphenyl)-2,2-difluoro-trans-4-n-propylcyclohexane.

The same method is used to prepare:
1-(p-butylphenyl)-2,2-difluoro-4-propylcyclohexane
1-(p-propylphenyl)-2-2-difluoro-4-propylcyclohexane
1-(p-ethylphenyl)-2,2-difluoro-4-propylcyclohexane
1-(p-methoxyphenyl)-2,2-difluoro-4-propylcyclohexane
1-(p-ethoxyphenyl)-2,2-difluoro-4-propylcyclohexane
1-(p-propoxyphenyl)-2,2-difluoro-4-propylcyclohexane
1-(p-cyanophenyl)-2,2-difluoro-4-propylcyclohexane 1-(p-butylphenyl)-2,2-difluoro-4-butylcyclohexane
1-(p-propylphenyl)-2,2-difluoro-4-butylcyclohexane
1-(p-ethylphenyl)-2,2-difluoro-4-butylcyclohexane
1-(p-methoxyphenyl)-2,2-difluoro-4-butylcyclohexane
1-(p-ethoxyphenyl)-2,2-difluoro-4-butylcyclohexane
1-(p-propoxyphenyl)-2,2-difluoro-4-butylcyclohexane
1-(p-cyanophenyl)-2,2-difluoro-4-butylcyclohexane 1-(p-butylphenyl)-2,2-difluoro-4-pentylcyclohexane
1-(p-propylphenyl)-2,2-difluoro-4-pentylcyclohexane
1-(p-ethylphenyl)-2,2-difluoro-4-pentylcyclohexane
1-(p-methoxyphenyl)-2,2-difluoro-4-pentylcyclohexane
1-(p-ethoxyphenyl)-2,2-difluoro-4-pentylcyclohexane
1-(p-propoxyphenyl)-2,2-difluoro-4-pentylcyclohexane
1-(p-cyanophenyl)-2,2-difluoro-4-pentylcyclohexane

EXAMPLE 18

A mixture of 28.8 g of trans-4-n-propyl-2-hydroxy-1-(p-pentylphenyl)-cyclohexane [obtainable from the corresponding ketone by reduction with $LiAlH_4$] and 2.4 g of NaH in 150 ml of dimethoxyethane is heated to 60° under an $N_2$ atmosphere. 13 g of dimethyl sulfate are then gradually added with vogorous stirring, and stirring is continued for 12 hours. The reaction product is worked up as customary and the product purified by chromatography to give r-1-(p-n-pen-tylphenyl)-2-methoxy-trans-4-n-propylcyclohexane.

The same method is used to prepare:
1(p-butylphenyl)-2-methoxy-4-propylcyclohexane
1-(p-propylphenyl)-2-methoxy-4-propylcyclohexane
1-(p-ethylphenyl)-2-methoxy-4-propylcyclohexane
1-(p-methoxyphenyl)-2-methoxy-4-propylcyclohexane
1-(p-ethoxyphenyl)-2-methoxy-4-propylcyclohexane
1-(p-propoxyphenyl)-2-methoxy-4-propylcyclohexane
1-(p-cyanophenyl)-2-methoxy-4-propylcyclohexane 1-(p-butylphenyl)-2-methoxy-4-butylcyclohexane
1-(p-propylphenyl)-2-methoxy-4-butylcyclohexane
1-(p-ethylphenyl)-2-methoxy-4-butylcyclohexane 1-(p-methoxyphenyl)-2-methoxy-4-butylcyclohexane
1-(p-ethoxyphenyl)-2-methoxy-4-butylcyclohexane
1-(p-propoxyphenyl)-2-methoxy-4-butylcyclohexane
1-(p-cyanophenyl)-2-methoxy-4-butylcyclohexane 1-(p-butylphenyl)-2-methoxy-4-pentylcyclohexane
1-(p-propylphenyl)-2-methoxy-4-pentylcyclohexane
1-(p-ethylphenyl)-2-methoxy-4-pentylcyclohexane
1-(p-methoxyphenyl)-2-methoxy-4-pentylcyclohexane
1-(p-ethoxyphenyl)-2-methoxy-4-pentylcyclohexane
1-(p-propoxyphenyl)-2-methoxy-4-pentylcyclohexane
1-(p-cyanophenyl)-2-methoxy-4-pentylcyclohexane

EXAMPLE 19

65 g of $POCl_3$ are added dropwise with stirring at 50° to a solution of 24 g of 2-(p-ethylphenyl)-5-n-propylcyclohexanecarboxamide in 500 ml of DMF. After further stirring for one hour the reaction mixture is poured onto ice and worked up as customary to give 2-(p-ethylphenyl)-5-n-propylcyclohexanecarbonitrile.

The same method is used to prepare:
2-(p-propylphenyl)-5-propylcyclohexanecarbonitrile
2-(p-butytphenyl)-5-propylcyclohexanecarbonitrile
2-(p-pentylphenyl)-5-propylcyclohexanecarbonitrile 2-(p-ethylphenyl)-5-butylcyclohexanecarbonitrile
2-(p-propylphenyl)-5-butylcyclohexanecarbonitrile
2-(p-butylphenyl)-5-butylcyclohexanecarbonitrile
2-(p-pentylphenyl)-5-butylcyclohexanecarbonitrile 2-(p-ethylphenyl)-5-pentylcyclohexanecarbonitrile
2-(p-propylphenyl)-5-pentylcyclohexanecarbonitrile
2-(p-butylphenyl)-5-pentylcyclohexanecarbonitrile
2-(p-pentylphenyl)-5-pentylcyclohexanecarbonitrile

EXAMPLE 20

0.01 mol of p-cyanophenol in 15 ml of pyridine is added to a solution of 0.01 mol of r-2-methyl-trans-4-n-propylcyclohexane-cis-1-carbonyl chloride [obtainable by literature methods from cis-3-methyl-4-carboxycyclohexanone (described in Chem. Ber. 116 (5), 1180 (1983))] in 10 ml of pyridine, and the reaction mixture is stirred at 0° for 20 hours and worked up as customary to give p-cyanophenyl r-2-methyl-trans-4-n-propylcyclohexane-cis-1-carboxylate.

The same method is used to prepare:

p-ethylphenyl r-2-methyl-trans-4-propylcyclohexane-cis-1-carboxylate
p-propylphenyl r-2-methyl-trans-4-propylcyclohexane-cis-1-carboxylate
p-butylphenyl r-2-methyl-trans-4-propylcyclohexane-cis-1-carboxylate
p-pentylphenyl r-2-methyl-trans-4-propylcyclohexane-cis-1-carboxylate
p-methoxyphenyl r-2-methyl-trans-4-propylcyclohexane-cis-1-carboxylate
p-ethoxyphenyl r-2-methyl-trans-4-propylcyclohexane-cis-1-carboxylate
p-propoxyphenyl r-2-methyl-trans-4-propylcyclohexane-cis-1-carboxylate
p-butoxyphenyl r-2-methyl-trans-4-propylcyclohexane-cis-1-carboxylate p-ethylphenyl r-2-methyl-trans-4-butylcyclohexane-cis-1-carboxylate
p-propylphenyl r-2-methyl-trans-4-butylcyclohexane-cis-1-carboxylate
p-butylphenyl r-2-methyl-trans-4-butylcyclohexane-cis-1-carboxylate
p-pentylphenyl r-2-methyl-trans-4-butylcyclohexane-cis-1-carboxylate
p-methoxyphenyl r-2-methyl-trans-4-butylcyclohexane-cis-1-carboxylate
p-ethoxyphenyl r-2-methyl-trans-4-butylcyclohexane-cis-1-carboxylate
p-propoxyphenyl r-2-methyl-trans-4-butylcyclohexane-cis-1-carboxylate
p-butoxyphenyl r-2-methyl-trans-4-butylcyclohexane-cis-1-carboxylate
p-cyanophenyl r-2-methyl-trans-4-butylcyclohexane-cis-1-carboxylate p-ethylphenyl r-2-methyl-trans-4-pentylcyclohexane-cis-1-carboxylate
p-propylphenyl r-2-methyl-trans-4-pentylcyclohexane-cis-1-carboxylate
p-butylphenyl r-2-methyl-trans-4-pentylcyclohexane-cis-1-carboxylate
p-pentylphenyl r-2-methyl-trans-4-pentylcyclohexane-cis-1-carboxylate
p-methoxyphenyl r-2-methyl-trans-4-pentylcyclohexane-cis-1-carboxylate
p-ethoxyphenyl r-2-methyl-trans-4-pentylcyclohexane-cis-1-carboxylate
p-propoxyphenyl r-2-methyl-trans-4-pentylcyclohexane-cis-1-carboxylate
p-butoxyphenyl r-2-methyl-trans-4-pentylcyclohexane-cis-1-carboxylate
p-cyanophenyl r-2-methyl-trans-4-pentylcyclohexane-cis-1-carboxylate

EXAMPLE 21

(a) 105 g of 2,4,6-triisopropylbenzenesulfonyl hydrazide are added to a solution of 36 g of 3-methylcyclohexanone in 630 ml of THF, and the mixture is stirred at room temperature for 2 hours. 450 ml of methanol and 65 g of KCN are then added, and the mixture is heated under reflux for 2 hours. Customary working up and subsequent fractional distillation gives 3-methylcyclohexacarbonit-rile [sic].

(b) A solution of 17 g of 3-methylcyclohexanecarbonitrile in 140 ml of THF has added to it, at −78°, a lithium diisopropylamide solution (prepared from 140 ml of THF, 16 g of diisopropylamine and 100 ml of 1.6-molar butyllithium solution in hexane), followed, after 2 hours, by 25 g of diethyl carbonate, and stirring is continued for one hour. After heating to room temperature and pouring onto 300 ml of ice-water the mixture is neutralized with dilute hydrochloric acid. Customary working up and distillation gives ethyl 3-methyl-1-cyanocyclohexanecarboxylate.

This ester is hydrolyzed by heating with ethanolic potassium hydroxide solution. Neutralization, extraction with methyl tert.-butyl ether and distillative removal of the solvent gives 1-cyano-3-methylcyclohexanecarboxylic acid.

(c) A solution of 23 g of dicyclohexylcarbodiimide in 50 ml of $CH_2Cl_2$ is added at room temperature to a mixture of 16 g of 1-cyano-3-methyl-cyclohexanecarboxylic acid, 25 g of 4′-hexylbiphenyl-4-ol, 1.2 g of 4-diethylaminopyridine and 200 ml of methylene chloride, and the mixture is stirred for 2 hours. Customary working up and separation by column chromatography (silica gel/toluene) and recrystallization gives the pure product 4′-hexylbiphenyl-4-yl 1-cyano-3-methylcyclohex-anecarboxylate, m.p. 51°.

The same method is used to prepare:

4′-ethylbiphenyl-4-yl 1-cyano-3-methylcyclohexanecarboxylate
4′-propylbiphenyl-4-yl 1-cyano-3-methylcyclohexanecarboxylate
4′-butylbiphenyl-4-yl 1-cyano-3-methylcyclohexanecarboxylate
4′-pentylbiphenyl-4-yl 1-cyano-3-methylcyclohexanecarboxylate
4′-heptylbiphenyl-4-yl 1-cyano-3-methylcyclohexanecarboxylate
4′-ethoxybiphenyl-4-yl 1-cyano-3-methylcyclohexanecarboxylate
4′-propoxybiphenyl-4-yl 1-cyano-3-methylcyclohexanecarboxylate
4′-butoxybiphenyl-4-yl 1-cyano-3-methylcyclohexanecarboxylate
4′-pentoxybiphenyl-4-yl 1-cyano-3-methylcyclohexanecarboxylate
4′-hexoxybiphenyl-4-yl 1-cyano-3-methylcyclohexanecarboxylate
4′-heptoxybiphenyl-4-yl 1-cyano-3-methylcyclohexanecarboxylate 4′-ethylbiphenyl-4-yl 1-cyano-3-ethylcyclohexanecarboxylate
4′-propylbiphenyl-4-yl 1-cyano-3-ethylcyclohexanecarboxylate
4′-butylbiphenyl-4-yl 1-cyano-3-ethylcyclohexanecarboxylate
4′-pentylbiphenyl-4-yl 1-cyano-3-ethylcyclohexanecarboxylate 4'-hexylbiphenyl-4-yl 1-cyano-3-ethylcyclohexanecarboxylate 4'-heptylbiphenyl-4-yl 1-cyano-3-ethylcyclohexanecarboxylate 4'-ethoxybiphenyl-4-yl 1-cyano-3-ethylcyclohexanecarboxylate 4'-propoxybiphenyl-4-yl 1-cyano-3-ethylcyclohexanecarboxylate 4'-butoxybiphenyl-4-yl 1-cyano-3-ethylcyclohexanecarboxylate 4'-pentoxybiphenyl-4-yl 1-cyano-3-ethylcyclohexanecarboxylate 4'-hexoxybiphenyl-4-yl 1-cyano-3-ethylcyclohexanecarboxylate 4'-heptoxybiphenyl-4-yl 1-cyano-3-ethylcyclohexanecarboxylate 4'-ethylbiphenyl-4-yl 1-cyano-3-chlorocyclohexanecarboxylate 4'-propylbiphenyl-4-yl 1-cyano-3-chlorocyclohexanecarboxylate 4'-butylbiphenyl-4-yl 1-cyano-3-chlorocyclohexanecarboxylate 4'-pentylbiphenyl-4-yl 1-cyano-3-chlorocyclohexanecarboxylate 4'-hexylbiphenyl-4-yl 1-cyano-3-chlorocyclohexanecarboxylate 4'-heptylbiphenyl-4-yl 1-cyano-3-chlorocyclohexanecarboxylate 4'-ethoxybiphenyl-4-yl 1-cyano-3-chlorocyclohexanecarboxylate 4'-propoxybiphenyl-4-yl 1-cyano-3-chlorocyclohexanecarboxylate 4'-butoxybiphenyl-4-yl 1-cyano-3-chlorocyclohexanecarboxylate 4'-pentoxybiphenyl-4-yl 1-cyano-3-chlorocyclohexanecarboxylate 4'-hexoxybiphenyl-4-yl 1-cyano-3-chlorocyclohexanecarboxylate 4'-heptoxybiphenyl-4-yl 1-cyano-3-chlorocyclohexanecarboxylate

EXAMPLE 22

A mixture of 3.1 g of 3-methylcyclohexanecarbonitrile and 30 ml of THF has added to it at −78° a solution of lithium diisopropylamide (prepared from 3.3 g of diisopropylamine, 30 ml of THF and 19 ml of 1.6-molar butyllithium solution in hexane) and then a solution of 9.7 g of 1-bromo-2-(4'-pentylbiphenyl-4-yl)ethane in 30 ml of THF. Working up as in Example 1 gives 1-(1-cyano-3-methylcyclohexyl)-2-(4'-pentylbiphenyl-4-yl)ethane, m.p. 73°.

The same method is used to prepare:

1-(1-cyano-3-methylcyclohexyl)-2-(4'-ethylbiphenyl-4-yl)-ethane 1-(1-cyano-3-methylcyclohexyl)-2-(4'-propylbiphenyl-4-yl)-ethane 1-(1-cyano-3-methylcyclohexyl)-2-(4'-butylbiphenyl-4-yl)-ethane 1-(1-cyano-3-methylcyclohexyl)-2-(4'-hexylbiphenyl-4-yl)-ethane 1-(1-cyano-3-methylcyclohexyl)-2-(4'-heptylbiphenyl-4-yl)-ethane 1-(1-cyano-3-methylcyclohexyl)-2-(4'-ethoxybiphenyl-4-yl)-ethane 1-(1-cyano-3-methylcyclohexyl)-2-(4'-propoxybiphenyl-4-yl)-ethane 1-(1-cyano-3-methylcyclohexyl)-2-(4'-butoxybiphenyl-4-yl)-ethane 1-(1-cyano-3-methylcyclohexyl)-2-(4'-pentoxybiphenyl-4-yl)-ethane 1-(1-cyano-3-methylcyclohexyl)-2-(4'-hexoxybiphenyl-4-yl)-ethane 1-(1-cyano-3-methylcyclohexyl)-2-(4'-heptoxybiphenyl-4-yl)-ethane 1-(1-cyano-3-ethylcyclohexyl)-2-(4'-ethylbiphenyl-4-yl)-ethane 1-(1-cyano-3-ethylcyclohexyl)-2-(4'-propylbiphenyl-4-yl)-ethane 1-(1-cyano-3-ethylcyclohexyl)-2-(4'-butylbiphenyl-4-yl)-ethane 1-(1-cyano-3-ethylcyclohexyl)-2-(4'-pentylbiphenyl-4-yl)-ethane 1-(1-cyano-3-ethylcyclohexyl)-2-(4'-hexylbiphenyl-4-yl)-ethane 1-(1-cyano-3-ethylcyclohexyl)-2-(4'-heptylbiphenyl-4-yl)-ethane 1-(1-cyano-3-ethylcyclohexyl)-2-(4'-ethoxybiphenyl-4-yl)-ethane 1-(1-cyano-3-ethylcyclohexyl)-2-(4'-propoxybiphenyl-4-yl)-ethane 1-(1-cyano-3-ethylcyclohexyl)-2-(4'-butoxybiphenyl-4-yl)-ethane 1-(1-cyano-3-ethylcyclohexyl)-2-(4'-pentoxybiphenyl-4-yl)-ethane 1-(1-cyano-3-ethylcyclohexyl)-2-(4'-hexoxybiphenyl-4-yl)-ethane 1-(1-cyano-3-ethylcyclohexyl)-2-(4'-heptoxybiphenyl-4-yl)-ethane

EXAMPLE 23

The method of Example 22 is used to obtain 1-(1-cyano-3-methylcyclohexyl)-2-[4-(4-pentylcyclohexyl)-phenyl-1-yl]-ethane, m.p. 92°, by reacting 1-bromo-2-[4-(4-pentylcyclohexyl)phenyl-1-yl]-ethane with 3-methylcyclohexanecarbonitrile.

The same method is used to prepare:

1-(1-cyano-3-methylcyclohexyl)-2-[4-(4-ethylcyclohexyl)-phenyl-1-yl]ethane 1-(1-cyano-3-methylcyclohexyl)-2-[4-(4-propylcyclohexyl)-phenyl-1-yl]ethane 1-(1-cyano-3-methylcyclohexyl)-2-[4-(4-butylcyclohexyl)-phenyl-1-yl]ethane 1-(1-cyano-3-methylcyclohexyl)-2-[4-(4-hexylcyclohexyl)-phenyl-1-yl]ethane 1-(1-cyano-3-methylcyclohexyl)-2-[4-(4-heptylcyclohexyl)-phenyl-1-yl]ethane There now follow examples of liquid-crystalline phases containing at least one compound of the formula I:

EXAMPLE A

The liquid-crystalline phase prepared comprises:

17% of p-(trans-4-propylcyclohexyl)-benzonitrile,

22% of p-(trans-4-butylcyclohexyl)-benzonitrile,

24% of p-(trans-4-pentylcyclohexyl)-benzonitrile,

14% of p-(trans-4-heptylcyclohexyl)-benzonitrile,

18% of 4-ethyl-4'-(trans-4-pentylcyclohexyl)-biphenyl and

15% of 2-methyl-1-(p-pentylphenyl)-4-(trans-4-propyl-cyclohexyl)-cyclohexane.

EXAMPLE B

The liquid-crystalline phase prepared comprises

16% of trans-1-(p-ethoxyphenyl)-4-propylcyclohexane,

12% of trans-1-(p-butoxyphenyl)-4-propylcyclohexane,
16% of p-(trans-4-propylcyclohexyl)-benzonitrile,
23% of p-(trans-4-pentylcyclohexyl)-benzonitrile,
15% of p-(trans-4-heptylcyclohexyl)-benzonitrile and
18% of 2-methyl-1-(p-pentylphenyl)-4-(trans-4-propyl-cyclohexyl)-cyclohexane.

What is claimed is:

1. A liquid crystalline phase having at least two liquid crystalline components, wherein at least one component is a compound of the formula I $$R^1\text{-}A^1\text{-}Z^1\text{-}A^2\text{-}R^2 \qquad \text{I}$$

in which $R^1$ and $R^2$ are each independently alkyl of 1–10 C atoms, in which one or two non-adjacent $CH_2$ groups can be replaced by O atoms and/or —CO— groups and/or —CO—O— groups and/or —CH=CH— groups, or one of $R^1$ and $R^2$ can also be F, Cl, Br, CN or $R^3\text{-}A^3\text{-}Z^2\text{-}$, $A^1$ is -A-, $A^4$-A- or -A-$A^4$-, A is a group of the formula (B) or (G)

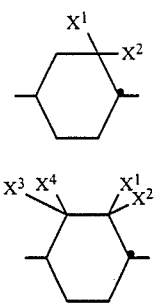

in which $X^1$, $X^2$, $X^3$ and $X^4$ are each, independently of one another, F, Cl, CN, —$CH_3$, —$CH_2CH_3$ or —$OCH_3$, wherein the groups of the formulae (B) and (G) can also have an additional substituent Q in the 1- or 4-position, Q being F, CN or $CH_3$, $A^2$, $A^3$ and $A^4$ are each independently 1,4-phenylene which is unsubstituted or substituted by one or two F and/or Cl atoms and/or $CH_3$ groups and/or CN groups, and in which one or two CH groups can also be replaced by N atoms and/or NO; 1,4-cyclohexylene in which one or two non-adjacent $CH_2$ groups can also be replaced by O atoms; or 1,3-dithiane-2,5-diyl, piperidine-1,4-diyl, decahydronaphthalene-2,6-diyl or 1,2,3,4-tetrahydronaphthalene-2,6-diyl groups, $Z^1$ and $Z^2$ are each independently —CO—O—, —O—CO—, —$CH_2CH_2$—, —$OCH_2$—, —$CH_2O$ or a single bond, and $R^3$ is H, alkyl of 1–10 C atoms, in which one or two non-adjacent $CH_2$ groups can be replaced by O atoms and/or —CO— groups and/or —CO—O— groups and/or —CH=CH— groups, or $R^3$ is F, Cl, Br or CN.

2. A phase according to claim 1, wherein $X^1$, $X^2$, $X^3$ and $X^4$ are each F.

3. A phase according to claim 1, wherein A is a group of formula (B).

4. A phase according to claim 1, wherein $R^1$ and $R^2$ are each methyl, ethyl, propyl, butyl, pentyl, hexyl, heptyl, octyl, nonyl, methoxy, ethoxy, propoxy, butoxy, pentoxy, hexoxy, heptoxy, octoxy, nonoxy, 2-methoxymethyl, ethoxymethyl or 2-methoxypenyl, 2-, 3- or 4-oxapentyl, 2-, 3-, 4- or 5-oxahexyl, 2-, 3-, 4-, 5- or 6-oxaheptyl, and one of $R^1$ and $R^2$ may also be F, Cl or CN.

5. A phase according to claim 1, wherein $A^2$, $A^3$ and $A^4$ are each independently 1,4-phenylene or 1,4-cyclohexylene.

6. A phase according to claim 1, wherein $Z^1$ and $Z^2$ are each independently single bonds, —O—CO—, —CO—O— or —$CH_2CH_2$— groups.

7. In a liquid crystal display element comprising a liquid crystalline phase, the improvement wherein the phase is one according to claim 1.

8. In an electrooptical display element comprising a liquid crystalline dielectric, the improvement wherein the dielectric is a phase according to claim 1.

* * * * *

UNITED STATES PATENT AND TRADEMARK OFFICE
CERTIFICATE OF CORRECTION

PATENT NO. : 4,846,998

DATED : JULY 11, 1989

INVENTOR(S) : POHL et al.

It is certified that error appears in the above-identified patent and that said Letters Patent is hereby corrected as shown below:

Title Page

Under the Abstract; Line 11

Delete (can be) Insert is

Col. 1, line 11,

Delete (can be) Insert is

Signed and Sealed this

Thirtieth Day of March, 1993

*Attest:*

STEPHEN G. KUNIN

*Attesting Officer*     *Acting Commissioner of Patents and Trademarks*